United States Patent [19]

Francoeur et al.

[11] Patent Number: 5,023,085
[45] Date of Patent: Jun. 11, 1991

[54] TRANSDERMAL FLUX ENHANCERS IN COMBINATION WITH IONTOPHORESIS IN TOPICAL ADMINISTRATION OF PHARMACEUTICALS

[75] Inventors: Michael L. Francoeur, East Lyme; Russell O. Potts, Old Saybrook, both of Conn.

[73] Assignee: Pfizer Inc., New York, N.Y.

[21] Appl. No.: 443,699

[22] Filed: Nov. 29, 1989

[51] Int. Cl.$^5$ .............................................. A61F 13/00
[52] U.S. Cl. .................... 424/449; 514/946; 514/947; 604/20
[58] Field of Search ................ 424/449; 514/946, 947; 604/20

[56] References Cited

U.S. PATENT DOCUMENTS

| | | | |
|---|---|---|---|
| 3,989,816 | 11/1976 | Rajadhyaksha | 424/60 |
| 3,991,755 | 11/1976 | Vernon | 128/172.1 |
| 4,316,893 | 2/1982 | Rajadhyaksha | 424/180 |
| 4,405,616 | 9/1983 | Rajadhyaksha | 424/244 |
| 4,557,934 | 12/1985 | Cooper | 424/128 |
| 4,919,648 | 4/1990 | Sibalis | 604/20 |
| 4,954,487 | 9/1990 | Cooper | 514/159 |

OTHER PUBLICATIONS

Cooper, Eugene R., J. Pharm. Sci., 73, 1153 (1984).
Tyle, Praveen, Pharm. Res. 3, 318 (1986).
Burnette, R. R. et al., J. Pharm. Sci., 75, 738 (1986).
Meyer, B. Robert et al., Am. J. Med. Sci., 297, 321 (1989).
Stoughton, Richard B., Arch. Derm. 118, 474 (1982).

*Primary Examiner*—Thurman Page
*Assistant Examiner*—D. Gabrielle Phelan
*Attorney, Agent, or Firm*—Peter C. Richardson; J. Trevor Lumb; Robert K. Blackwood

[57] ABSTRACT

Transdermal flux enhancers such as oleic acid and 1-dodecylazacycloheptan-2-one are used in combination with iontophoresis in the topical administration of pharmaceutical agents.

15 Claims, No Drawings

1

TRANSDERMAL FLUX ENHANCERS IN COMBINATION WITH IONTOPHORESIS IN TOPICAL ADMINISTRATION OF PHARMACEUTICALS

BACKGROUND OF THE INVENTION

This invention relates to the use of certain transdermal flux enhancers in combination with iontophoresis for the topical administration of pharmaceutical agents.

Many pharmaceutical agents are ionized. As a result, in conventional topical drug delivery systems, they are unable to adequately penetrate the skin surface, and so do not reach the desired site of action at therapeutic concentrations. With such ionic drugs, this problem has been partially solved by the process of iontophoresis. By this means, it has been possible to enhance the localized delivery of drug to tissue (e.g., dermis, muscle, bone joints, and the like) which is at or near the site of application. By this means, it has also been possible to transport the drug into the blood stream, thus providing systemic delivery of drug to the entire body.

According to the process of iontophoresis, an electric potential is applied across a localized portion of body tissue as a drug containing solution is held against the skin in that localized area. Sufficient potential is applied so as to cause a small current to pass through the solution and the adjacent body tissue. In this manner, the drug is "phoresed" from the solution across the dermal barrier and into the local tissue (to produce high local tissue levels of the drug), or given enough time and other appropriate conditions, into the blood stream, whereby the drug is delivered systemically to more remote site(s) of action. For a review of iontophoresis and iontophoretic devices, see Tyle, Pharm. Res., v. 3, pp. 318–326 (1986).

More recently, it has been shown in studies using mannitol that the flux of neutral, polar molecules is enhanced by iontophoresis, particularly in the presence of a cation such as $Na^+$, Burnette et al., J. Pharm. Sci., v. 75, pp. 738–743 (1986). See also Meyer et al., Am. J. Med. Sci., v. 296, pp. 321–324 (1989). Thus the flux of a pharmaceutical agent which is not ionized or even capable of ionization can also be increased by the local application of an electric potential.

In the topical administration of pharmaceutical agents, iontophoresis is primarily limited by two interrelated factors: (1) Transport through the skin generally occurs via appendages (e.g., hair follicles, sweat glands, etc.) or small "pores", which represent only a fraction of the total skin surface area. Consequently, these pathways are exposed to a very high charge density relative to the total applied current, leading to irreversible changes or damage. (2) Since the rate of drug delivery is proportional to the applied current, the magnitude of delivery is severely limited by the problem described in (1) above.

As an alternative method for enhancing the transdermal flux of pharmaceutical agents, a variety of so-called penetration enhancers have been proposed for use as adjuncts in the topical administration of pharmaceutical agents. For example, see U.S. Pat. Nos. 3,989,816, 4,316,893, 4,405,616, 4,537,776, 4,557,934; Stoughton, Arch. Derm. v. 118, pp. 474–477 (1982); Cooper, J. Pharm. Sci., v. 73, pp. 1153–1156 (1984); and Akhtesi et al., J. Pharm. Pharmacol. v. 36, p. 7P (1984).

Surprisingly, we have now found that the combination of iontophoresis with such transdermal flux enhancing agents leads to a synergistic effect in which flux across the dermal barrier is much higher than expected. This permits local and systemic delivery of a given amount of pharmaceutical agents by iontophoresis under much milder conditions of electrical potential and current density, avoiding the irreversible changes or damage to the skin noted above.

SUMMARY OF THE INVENTION

The present invention is directed to a method of treating a disease in a human or lower animal which comprises iontophoretic, topical administration of a pharmaceutical composition at reduced electric potential and current density. Accordingly, said composition comprises:

(a) a safe and effective amount of a pharmaceutical agent;

(b) an aqueous solvent; and (c) a transdermal flux enhancing amount of a dermal penetration enhancer which is a 1-alkylazacycloheptan-2-one, said alkyl having from 8 to 16 carbon atoms, or a cis-olefin of the formula

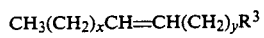

$$CH_3(CH_2)_xCH=CH(CH_2)_yR^3$$

where $R^3$ is $CH_2OH$, $CH_2NH_2$ or $COR^4$, and $R^4$ is OH or $(C_1-C_4)$alkoxy, x and y are each an integer from 3 to 13 and the sum of x and y is from 10 to 16.

Preferred dermal penetration enhancers are cis-9-tetradecenoic acid, cis-6-pentadecenoic acid, cis-6-hexadecenoic acid, cis-9-hexadecenoic acid, cis-9-octadecenoic acid (oleic acid), cis-6-octadecenoic acid, cis-11-octadecenoic acid, cis-12-octadecenoic acid, cis-5-eicosenoic acid, cis-9-eicosenoic acid, cis-11-eicosenoic acid, cis-14-eicosenoic acid, 1-decylazacycloheptan-2-one, 1-dodecylazacycloheptan-2-one or 1-tetradecylazacycloheptan-2-one. Most preferred is oleic acid.

The expression "aqueous solvent" refers to water itself as solvent, or a solvent which comprises, in addition to water, a water miscible organic solvent such as methanol, ethanol, isopropyl alcohol, propylene glycol, polyethylene glycol or glycerin.

The present method is generally useful with neutral pharmaceutical agents which are not capable of ionization, particularly neutral agents which are polar in nature. However, this method finds its preferred use in the case of pharmaceutical agents which are ionized, or capable of ionization. This is true regardless of whether high drug levels are desired near the site of application (as is frequently the case, for example, in treating localized pain or inflammation, or a localized bacterial or fungal infection), or systemic delivery of the drug to more remote locations is desired (as is generally the case, for example, in the treatment of cardiovascular conditions, systemic infections, CNS conditions or diabetes).

The present method is of particular value with (a) analgesic or antiinflammatory agents used in the treatment of pain or an inflammatory disease, particularly aspirin, acetaminophen, indomethacin, ibuprofen, naproxen, the compound of the formula (d) agents used in the treatment of cardiovascular diseases, particularly nifedipine, amlodipine, prazosin, doxazosin and the compounds of the formula

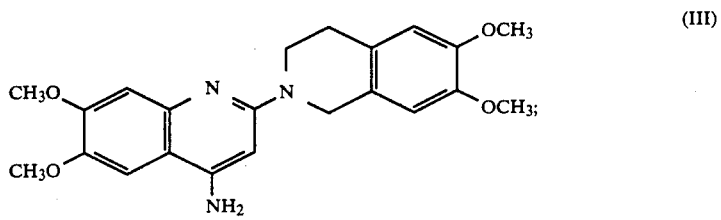

(III)

or

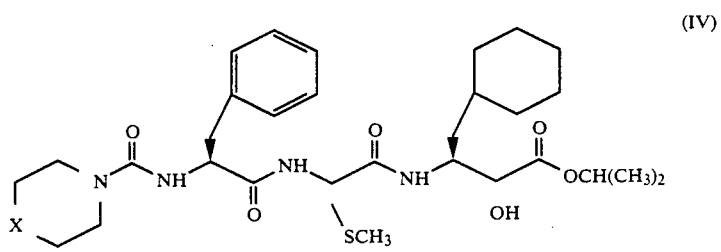

(IV)

wherein X is O or C=O; and the pharmaceutically acceptable salts thereof.

The present method is also of particular value with the pharmaceutical agents sertraline (used in the treatment of depression) and insulin, glipizide, the compound of the formula

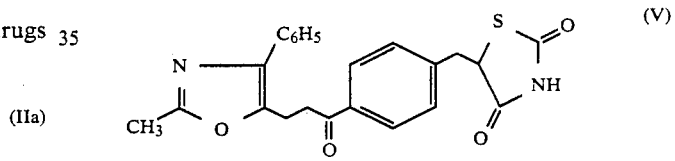

(V)

and the compound of the formula

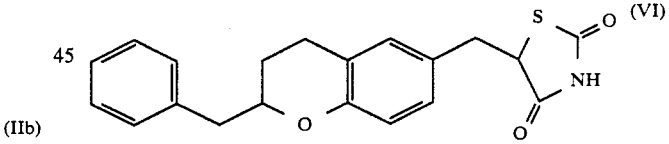

(VI)

(used in the treatment of diabetes); and the pharmaceutically acceptable salts thereof.

DETAILED DESCRIPTION OF THE INVENTION

The present invention is readily carried out. Accordingly, a pharmaceutical agent, dissolved in an aqueous solvent in the presence of a conventional penetration enhancer, as defined above, is topically administered using a conventional iontophoretic device (for examples, see Tyle, cited above). In some instances, the solution of the pharmaceutical agent will also contain a pharmaceutically acceptable ionized salt, such as sodium chloride and/or buffering constituents. The presence of an ionic salt is particularly valuable when an ionizable pharmaceutical agent is administered at a pH at which the agent is largely in unionized form, and is generally essential when the pharmaceutical agent is not capable of ionization.

(I)

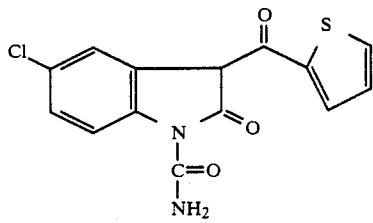

(generically named tenidap), piroxicam, and prodrugs of prioxicam of the formulas (IIa)

and (IIb)

wherein R is $CH(R^1)OCOR^2$ or $CH(R^1)OCOOR^2$, $R^1$ is hydrogen or methyl and $R^2$ is $(C_1-C_9)$ alkyl; and the pharmaceutically acceptable salts thereof;

(b) antifungal agents used in the treatment of a fungal infection, particularly fluconazole and tioconazole, and the pharmaceutically acceptable salts thereof;

(c) antibacterial agents used in the treatment of bacterial infections, particularly erythromycin, azithromycin, oxytetracycline, tetracycline, doxycycline, penicillin G, penicillin V, ampicillin and amoxicillin; and the pharmaceutically acceptable salts thereof; and The dose of the drug, as well as the concentration of the drug in the aqueous solution and the volume of the solution, will, of course, depend upon the particular pharmaceutical agent administered and upon whether local or full systemic delivery of the drug is intended. In general, when systemic delivery is intended, the dose of the pharmaceutical agent will correspond approximately to that which is employed in the more conventional oral or parenteral route. Of course, when gastrointestinal absorption of a particular pharmaceutical agent is known to be poor, it will be possible to obtain high systemic levels of the pharmaceutical agent by the present iontophoretic methods with relatively lower doses of the pharmaceutical agent.

Typical unit dosages of pharmaceutical agents administered according to the present method, based upon use in an adult of about 50 to 80 Kg weight, are as follows: doxazosin, 1-25 mg; the compound of formula (I) above, 20-200 mg; aspirin, 200-1,000 mg; acetaminophen, 200-10,000 mg; indomethacin, 10-50 mg; ibuprofen, 200-1,000 mg; naproxen, 100-500 mg; the compound of the formula (III), 0.01-2 mg; piroxicam, 5-20 mg; fluconazole, 0.1-1 g; tioconazole, 0.1-1 g; erythromycin, 100-500 mg; azithromycin, 50-500 mg; oxytetracycline, 50-500 mg; tetracycline, 50-500 mg; doxycycline, 10-100 mg; penicillin G, 100,000-500,000 units; penicillin V, 100-500 mg; ampicillin, 100-500 mg; amoxicillin, 100-500 mg; nifedipine, 5-20 mg; amolodipine, 1-25 mg; prazosin, 0.25-1.25 mg; the compound of the formula (IV) wherein X is O, 1-10 mg; the compound of the formula (IV) wherein X is C=O, 1-10 mg; insulin, 50-1,000 units; glipizide, 2.5-10 mg; the compound of the formula (V), 1-20 mg; the compound of the formula (VI), 1-20 mg; and sertraline, 1-20 mg. However, in particular circumstances, doses outside of these ranges will be used at the discretion of the attending physician.

When high localized concentrations of the desired drug are desired, the pharmaceutical agent will be administered iontophoretically, generally for a relatively short period of time, with the electric potential applied across the site where a high local concentration of the agent is desired; for example, with analgesics at the site of pain, with antiinflammatory agents at the site of inflammation, and with antibacterials or antifungals at the site of a localized infection.

On the other hand, when full systemic delivery of the pharmaceutical agent is desired, the site of administration is less critical. However, the site should be well supplied with blood vessels, so that the agent readily reaches the blood stream, which rapidly removes it from the site of administration and distributes it throughout the body. Generally, systemic delivery will require longer periods of iontophoresis, permitting maximal absorption and systemic delivery of the pharmaceutical agent.

According to the present method, the concentration of penetration enhancer employed is generally in the range of 0.01-5% (w/v), i.e., similar to the levels used absent iontophoresis. Preferred levels are generally in the range of about 0.1 to 1%. However, iontophoretic administration of pharmaceutical agents, according to the present method, is generally achieved under much milder conditions of electric potential and current density, avoiding irreversible changes or damage to the skin which can occur at higher potentials and/or current densities.

The synergistic effect of iontophoresis and a skin penetration agent in moving a pharmaceutical agent across the dermal barrier is demonstrated by iontophoresis experiments detailed below.

The present invention is illustrated by the following examples. However, it should be understood that the invention is not limited to the specific details of these examples.

EXAMPLE 1

Influence of Oleic Acid on the Transport of Sodium Ion Across the Dermal Barrier by Iontophoresis The methods employed in iontophoresis experiments were substantially the same as those described by Burnette et al., J. Pharm. Sci., v. 76, pp. 765-773 (1987).

Diffusion cells (Side-Bi-Side ®; Crown Glass Company, Inc., Sommerville, N.J.) were used in all transport studies. A 0.64-cm$^2$ area of tissue membrane was exposed to the donor and receptor compartments of each diffusion cell. The reservoirs were magnetically stirred, water jacketed, and had volumes of 3.0 mL. Temperature control (37°±0.2° C.) was provided by a constant temperature bath (Haake A80) with an external circulator (American Scientific Products, McGaw Park, Ill.). Electrodes were made by lightly sanding Ag wires (99.9% purity; 4 cm × 1.0 mm) and placing them in a 1M HCl solution for 10 minutes at 50° C. The Ag wires were then rinsed with distilled water and plated with AgCl by applying a current of 0.20 mA (both the cathode and anode were Ag wires) through a 0.5M KCl solution for 12 hours. Subsequently, the Ag—AgCl wires were plated with platinum black by passing a 100-mA current (the cathode was the Ag—AgCl electrode and the anode was a Pt wire of 99.99% purity) for 3-5 minutes through a solution containing 0.66 mM $Pb(C_2H_3O_2)_2$ and 0.073M $H_2PtCl_6$. The electrodes were positioned approximately 2 cm from either side of the tissue membrane, with the anode placed on the epidermal side and the cathode on the dermal side. The constant current required in the iontophoretic experiments was obtained from a programmable constant current source (model 224; Keithley Instruments, Inc., Cleveland, Ohio). Slight pH changes during iontophoresis were monitored (Digi-pH-ase LED pH meter equipped with an extra-slender neck, glass-body combination electrode, Cole Parmer, Ill.) and corrected for by the addition of microliter amounts of 1M HCl or 1M NaOH solutions. These additions changed the overall Na$^+$ and Cl$^-$ concentrations by a few percent at most. By this technique the pH was kept to within ±0.1 pH unit of 7.4.

Excised porcine skin from freshly slaughtered pigs was obtained using a Padgett electrodermatome (Kansas City, Mo.) set at 0.8 mm thickness. A thickness of 0.8 mm was chosen because it could be reproducibly obtained with the dermatome and because it resulted in specimens which were generally intact. Each piece of tissue was examined for any gross morphological damage such as tears or holes under a stereomicroscope (Stereomaster II, Allied Fischer Scientific, Itasca, Ill.) at a magnification of ×30 and ×60 using both transmitted and reflected light for illumination. All tissue was obtained within 24 hours after death, positioned dermal side down on a piece of filter paper soaked with 0.9% NaCl, placed in a petri dish, stored at 4° C., and used approximately 12 hours later.

All chemicals were used as received and all solutions were made using distilled water which had been passed through a Barnstead PCS water purification system (which contains charcoal filter and a mixed-bed ion exchange resin, the resulting water having a pH of 6-8 and a resistance of 14-18 Mohm/cm). Transport studies were carried out using buffer solutions which were 3:2 by volume mixtures of 0.13M NaCl in 25 mM HEPES buffer and ethanol. All buffers were degassed prior to use by sonicating the buffer at 40° C. under reduced pressure in order to prevent bubble formation on the tissue, which could result in artifactual transport results. Radiotracer solutions were made up in the buffer $^{22}Na^+$ (0.3 μCi/mL) obtained from NEN Research Products (Boston, Mass.). In those experiments employing oleic acid, this compound was present at a level of 0.25% w/v in the buffer solution.

Transport studies were performed by mounting the excised tissue in the diffusion cell, placing plain buffer solution in the chamber adjacent to one side of the tissue, adding buffer containing tracer to the other chamber, inserting electrodes (if required), and turning on the magnetic stirrers. The starting time was defined as the time when the current was turned on, with samples being taken at 0.75-1.5 hour intervals for 8.25 hours. Samples of 2 mL were obtained by disconnecting the current source, removing the entire contents of the receiving cell, rinsing the receiving cell with fresh buffer, replacing with 3 mL of fresh buffer, and reconnecting the electrodes and current source. The $^{22}Na^+$ samples were counted in a auto-gamma scintillation spectrometer 5236 (Packard Instrument Company, Downers Grove, Ill.). The mean total counts obtained had standard errors of the mean (SEM) which were less than ±5% of the mean (n=3) except for the passive diffusion samples which were greater than ±5%.

Fluxes were calculated from the quantity of radioisotope transferred per unit time and the specific radioactivity in the donor compartment. (Control experiments showed that the free solution specific activity of the isotope in the donor chamber remained approximately constant throughout the course of an experiment. This implies that loss of isotope through transport into the receiving chamber or through absorption of isotope onto the glass or the electrodes was negligible.) The fluxes were expressed per unit area by dividing the flux by the surface area of the tissue (0.64 cm$^2$). These fluxes were defined to occur at a time equal to the total elapsed time minus one-half the collection time interval.

For the experiments whose results are shown in Table I, the anode and the Na$^+$ tracer were placed in the chamber facing the dermal side of the tissue. Control experiments show no significant passive flux of Na$^+$ absent electric current or oleic acid.

The synergistic effect of iontophoresis coupled with oleic acid is demonstrated by the data in Table II. The expected flux, which is the sum of the flux resulting from current alone and oleic acid alone, is generally well below that observed with combined use of current and oleic acid.

TABLE I

| Time (h) | OA$^a$ alone | Average Na$^+$ Flux (μmol/cm$^2$/h) | | | |
|---|---|---|---|---|---|
| | | Current alone | | OA$^a$ + Current | |
| | | 0.25 μAmp | 100 μAmp | 0.25 μAmp | 100 μAmp |
| 0.75 | 0.1 | 0.5 | 2.0 | 0.8 | 3.1 |
| 2.25 | 0.3 | 0.9 | 3.8 | 1.6 | 6.0 |
| 3.75 | 0.8 | 1.0 | 4.5 | 1.7 | 6.5 |

TABLE I-continued

| Time (h) | OA$^a$ alone | Average Na$^+$ Flux (μmol/cm$^2$/h) | | | |
|---|---|---|---|---|---|
| | | Current alone | | OA$^a$ + Current | |
| | | 0.25 μAmp | 100 μAmp | 0.25 μAmp | 100 μAmp |
| 5.25 | 1.0 | 1.0 | 5.0 | 2.1 | 7.4 |
| 6.75 | 1.3 | 1.3 | 5.0 | 2.5 | 7.5 |
| 8.25 | 1.7 | 1.2 | 5.2 | 2.6 | 8.2 |

$^a$Oleic Acid, 0.25%

TABLE II

| Time (h) | Additive Na$^+$ Versus Observed Flux with Oleic Acid and Current | | | |
|---|---|---|---|---|
| | 25 μAmp | | 100 μAmp | |
| | Calcd. | Observed | Calcd. | Observed |
| 0.75 | 0.6 | 0.8 | 2.1 | 3.1 |
| 2.25 | 1.2 | 1.6 | 4.1 | 6.0 |
| 3.75 | 1.8 | 1.7 | 5.3 | 6.5 |
| 5.25 | 2.0 | 2.1 | 6.0 | 7.4 |
| 6.75 | 2.6 | 2.5 | 6.3 | 7.5 |
| 8.25 | 2.9 | 2.6 | 6.9 | 8.2 |

EXAMPLE 2

Treatment of Hypertension with Doxazosin Using Iontophoresis and Oleic Acid

A. Apparatus—An electrical device capable of generating a constant current of from 0.1 to 9.0 mA using a power source of up to 10 volts. Two electrodes, anode and cathode made of appropriate material (e.g., Ag-/AgCl or platinum). The anode or positive electrode is a pliable reservoir (3-5 ml) with a semipermeable porous membrane for placement next to the skin. The cathode or return electrode is filled with a conductive gel.

B. Drug Solutions—Doxazosin (2-20 mg, as the mesylate salt) is dissolved in a 3-5 ml volume of 20-70% (v/v) ethanol vehicle. The vehicle also contains 5-100 mM of a phosphate buffer at pH 3-5 and 0.1-1% (w/v) of oleic acid.

C. Administration—The above solution of doxazosin is filled into the anode reservoir. The anode is afixed to the surface of the chest with adhesive while the return electrode is placed on an adjacent area. 0.1-5 mA of current is applied for 10-90 minutes until systemic delivery of the drug is sufficient to reduce blood pressure to the desired level.

EXAMPLE 3

Treatment of Muscle or Arthritic Joint Pain and Inflammation with Piroxicam Using Iontophoresis and Oleic Acid A. Background—This type of therapy is applicable to acute flare-ups or injury and is used in place of or in conjunction with oral therapy to enhance drug levels locally at the intended site.

B. Apparatus—Same as the preceding example, except that the cathode (−) is the drug electrode and the anode (+) is the return electrode.

C. Drug Solutions—Same as the preceding example, except that 1 mg/ml of piroxicam concentration at pH 7.4 is used.

D. Administration—Same as the preceding example, except electrodes are placed adjacent to site of injury or pain/inflammation.

We claim:

1. A method of treating a disease in a human or lower animal which comprises iontophoretic administration of a pharmaceutical composition comprising:
   (a) a pharmaceutically effective amount of an active agent;
   (b) an aqueous solvent; and
   (c) a transdermal flux enhancing amount of a dermal penetration enhancer which is selected from the group consisting of 1-alkylazacycloheptan-2-one, said alkyl having from 8 to 16 carbon atoms, and a cis-olefin of the formula $CH_3(CH_2)_xCH=CH(CH_2)_yR^3$ where $R^3$ is $CH_2OH$, $CH_2NH_2$ or $COR^4$, and $R^4$ is OH or $(C_1-C_4)$alkoxy, x and y are each an integer from 3 to 13 and the sum of x and y is from 10 to 16.

2. A method according to claim 1 wherein the dermal penetration enhancer is selected from the group consisting of cis-9-tetradecenoic acid, cis-6-pentadecenoic acid, cis-6-hexadecenoic acid, cis-9-hexadecenoic acid, cis-9-octadecenoic acid (oleic acid), cis-6-octadecenoic acid, cis-11-octadecenoic acid, cis-12-octadecenoic acid, cis-5-eicosenoic acid, cis-9-eicosenoic acid, cis-11-eicosenoic acid, cis-14-eicosenoic acid, 1-decylazacycloheptan-2-one, 1-dodecylazacycloheptan-2-one and 1-tetradecylazacycloheptan-2-one.

3. A method according to claim 2 wherein the dermal penetration enhancer is cis-9-octadecenoic acid.

4. A method according to claim 1 wherein the aqueous solvent further comprises, in addition to water, methanol, ethanol, isopropyl alcohol, propylene glycol, polyethylene glycol or glycerin.

5. A method according to claim 1 wherein the active agent is an ionized or ionizable pharmaceutical agent.

6. A method of claim 5 wherein the pharmaceutical agent is an analgesic or antiinflammatory agent used in the treatment of pain or an inflammatory disease.

7. A method of claim 6 wherein the analgesic or antiinflammatory agent is selected from the group consisting of aspirin, acetaminophen, indomethacin, ibuprofen, naproxen, a compound of the formula

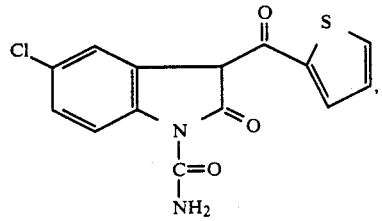

piroxicam, and prodrugs of piroxicam of the formula

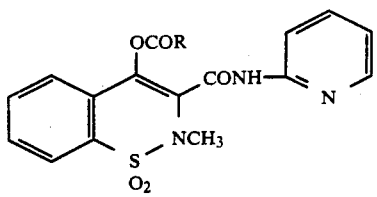

or

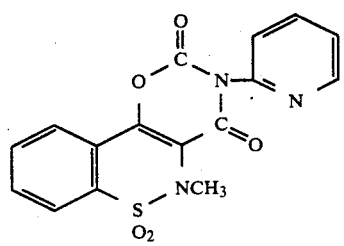

wherein R is $CH(R^1)OCOR^2$ or $CH(R^1)OCOOR^2$, $R^1$ is hydrogen or methyl and $R^2$ is $(C_1-C_9)$alkyl; or a pharmaceutically acceptable salt of said analgesic or antiinflammatory agents.

8. A method according to claim 5 wherein the pharmaceutical agent is an antibacterial agent used in the treatment of a bacterial infection.

9. A method of claim 8 wherein the antibacterial agent is selected from the group consisting of erythromycin, azithromycin, oxytetracycline, tetracycline, doxycycline, penicillin G, penicillin V, ampicillin and amoxicillin; or a pharmaceutically acceptable salt thereof.

10. A method according to claim 5 wherein the pharmaceutical agent is an antifungal agent used in the treatment of a fungal infection.

11. A method according to claim 10 wherein the antifungal agent is selected from the group consisting of fluconazole and tioconazole, or a pharmaceutically acceptable salt thereof.

12. A method of claim 5 wherein the pharmaceutical agent is used in the treatment of a cardiovascular disease.

13. A method of claim 12 wherein the pharmaceutical agent is selected from the group consisting of nifedipine, amlodipine, prazosin, doxazosin, a compound of the formula

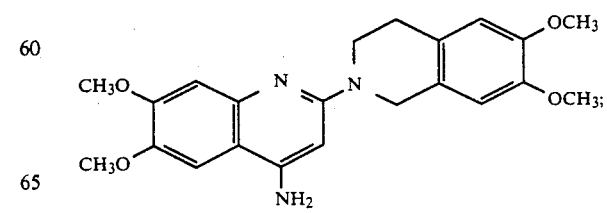

and a compound of the formula

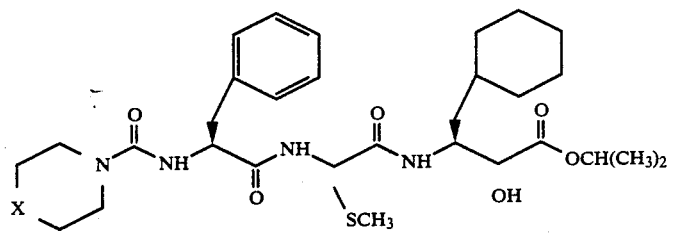

wherein X is O or C=O; or a pharmaceutically acceptable salt thereof.

14. A method of claim 5 wherein the pharmaceutical agent is selected from the group consisting of sertraline, insulin, glipizide, a compound of the formula

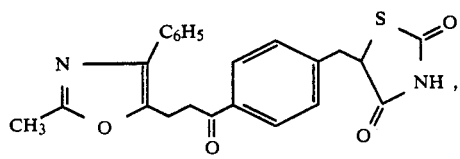

and a compound of the formula

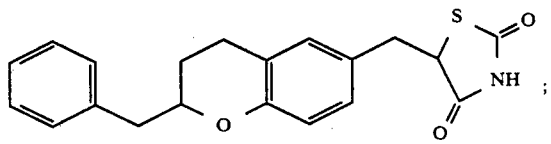

or a pharmaceutically acceptable salt thereof.

15. A method according to any one of claims 5 to 14 wherein the dermal penetration enhancer is cis-9-octadecenoic acid.

* * * * *